(12) United States Patent
Bhatti et al.

(10) Patent No.: US 8,984,583 B2
(45) Date of Patent: Mar. 17, 2015

(54) HEALTHCARE PRIVACY BREACH PREVENTION THROUGH INTEGRATED AUDIT AND ACCESS CONTROL

(71) Applicants: Rafae Bhatti, Sunnyvale, CA (US); Paul D. Martin, Baltimore, MD (US)

(72) Inventors: Rafae Bhatti, Sunnyvale, CA (US); Paul D. Martin, Baltimore, MD (US)

(73) Assignee: Accenture Global Services Limited, Dublin (IE)

( * ) Notice: Subject to any disclaimer, the term of this patent is extended or adjusted under 35 U.S.C. 154(b) by 30 days.

(21) Appl. No.: 13/800,883

(22) Filed: Mar. 13, 2013

(65) Prior Publication Data
US 2013/0326579 A1    Dec. 5, 2013

Related U.S. Application Data

(60) Provisional application No. 61/653,029, filed on May 30, 2012.

(51) Int. Cl.
| G06F 17/30 | (2006.01) |
| G06F 21/62 | (2013.01) |
| G06F 19/00 | (2011.01) |
| G06Q 10/06 | (2012.01) |

(Continued)

(52) U.S. Cl.
CPC .............. G06F 21/62 (2013.01); G06F 19/322 (2013.01); G06Q 10/06 (2013.01); G06Q 50/24 (2013.01); *G06F 19/3443* (2013.01); G06F 21/6245 (2013.01); *G06F 2221/2101* (2013.01)
USPC .......................... 726/1; 726/6; 726/18; 726/28

(58) Field of Classification Search
CPC ...... G06Q 10/06; G06Q 50/24; G06F 19/322; G06F 19/3443; G06F 21/6245; G06F 2221/2101

USPC ............................................. 726/1, 6, 18, 28
See application file for complete search history.

(56) References Cited

U.S. PATENT DOCUMENTS 6,278,977 B1 * 8/2001 Agrawal et al. .............. 705/7.27
6,516,315 B1 * 2/2003 Gupta ................................... 1/1

(Continued)

OTHER PUBLICATIONS

Bauer, Lujo, Scott Garriss, and Michael K. Reiter. "Detecting and resolving policy misconfigurations in access-control systems." ACM Transactions on Information and System Security (TISSEC) 14.1 (2011): 2.*

(Continued)

*Primary Examiner* — Michael Simitoski
(74) *Attorney, Agent, or Firm* — Finnegan, Henderson, Farabow, Garrett & Dunner, LLP

(57) ABSTRACT

A computer-implemented method for compliance with a privacy requirement. The method comprises analyzing, using one or more processors, an access log related to a history of users accessing records; deriving a plurality of roles assigned to the users and a plurality of accesses reflecting actions taken by the users; and deriving from the access log a mapped log comprising a plurality of mapping records including a plurality of mapped role-access pairs. The method further comprises generating, using the one or more processors, a reduced log including a plurality of reduced records comprising a mapped role-access pair and statistics that are associated with the mapped role-access pair, the statistics being derived from a subset of the mapping records that include the mapped role-access pair; and deriving an access policy based on the reduced log, wherein the access policy includes a plurality of proposed role-access pairs.

22 Claims, 9 Drawing Sheets

(51) Int. Cl.
*G06Q 50/24* (2012.01)
*G06F 7/04* (2006.01)

(56) References Cited

U.S. PATENT DOCUMENTS

| | | | | |
|---|---|---|---|---|
| 7,779,113 | B1* | 8/2010 | Samar | 709/224 |
| 8,041,749 | B2* | 10/2011 | Beck | 707/803 |
| 8,688,499 | B1* | 4/2014 | Bose et al. | 705/7.27 |
| 2004/0098594 | A1* | 5/2004 | Fleming et al. | 713/182 |
| 2008/0147610 | A1* | 6/2008 | Mohanty et al. | 707/3 |
| 2009/0300711 | A1* | 12/2009 | Tokutani et al. | 726/1 |
| 2011/0082716 | A1* | 4/2011 | Bhamidipaty et al. | 705/7.11 |
| 2011/0093293 | A1* | 4/2011 | G. N. et al. | 705/3 |
| 2012/0215560 | A1* | 8/2012 | Ofek et al. | 705/3 |
| 2013/0067538 | A1* | 3/2013 | Dharmarajan et al. | 726/4 |
| 2013/0104046 | A1* | 4/2013 | Casco-Arias Sanchez et al. | 715/736 |

OTHER PUBLICATIONS

Chung, Christina Yip, Michael Gertz, and Karl Levitt. "Demids: A misuse detection system for database systems." Integrity and Internal Control in Information Systems. Springer US, 2000. 159-178.*

Gunter, Carl A., David Liebovitz, and Bradley Malin. "Experience-based access management: A life-cycle framework for identity and access management systems." IEEE security & privacy 9.5 (2011): 48.*

Zhang, Wen, et al. "Role prediction using electronic medical record system audits." Proceedings of the 2nd USENIX conference on Health security and privacy. USENIX Association, 2011.*

J.A. Akinyele et.al., "Securing electronic medical records using attribute-based encryption on mobile devices", Proceedings of the 1st ACM workshop on Security and privacy in smartphones and mobile devices, Oct. 17, 2011, pp. 75-86, ACM New York, NY, USA.

R. Bhatti et.al., "Towards improved privacy policy coverage in healthcare using policy refinement." Proceedings of the 4th VLDB conference on Secure data management, SDM 2007, Sep. 23-24, 2007, pp. 158-173, Springer-Verlag Berlin, Heidelberg, 2007.

Wagner, M, *Electronic Medical Records: The Good, Bad, and Ugly*, DarkReading (Dec. 18, 2009), http://www.darkreading.com/government-vertical/electronic-medical-records-the-good-the-bad/222002718.

Saviynt EPIC Access Manager, Saviynt, http://www.saviynt.com/saviynt-for-epic/ (last visited Nov. 11, 2013).

Resources. Fairwarning, http://www.fairwarning.com/resources/resources#whitepapers (last visited Nov. 11, 2013).

* cited by examiner

| Role | | Access | user ID |
|---|---|---|---|
| Hematology | Fellow (Res) | Examroom View | 755361 |
| Hospital Medicine | Resident | Encounter View | 755050 |
| Hematology | Resident | Message Modify | 752717 |
| Cardiology | Nurse | Encounter View | 754828 |
| General Medicine | Fellow (Res) | OtherEnc View | 755328 |
| General Medicine | Fellow (Res) | OtherEnc View | 755328 |
| Hospital Medicine | Fellow (Res) | Encounter View | 752652 |
| General Medicine | Resident | OtherEnc View | 754876 |
| Gyne Oncology | Resident | OtherEnc View | 754902 |
| Gyne Oncology | Resident | OtherEnc View | 754902 |
| Pulmonary Med | Resident | Examroom Modify | 752708 |
| Cardiology | Fellow (Res) | OtherEnc View | 755244 |
| Cardiology | Fellow (Res) | OtherEnc View | 755244 |
| Hospital Medicine | Resident | Encounter Exit | 754881 |
| Hospital Medicine | Staff | OtherEnc View | 755333 |
| Hospital Medicine | Fellow (Res) | OtherEnc View | 755333 |
| General Medicine | Resident | Encounter View | 754718 |
| Transplant Surgery | Fellow (Res) | Encounter View | 755314 |
| Hospital Medicine | Resident | OtherEnc View | 754726 |
| General Medicine | Resident | OtherEnc View | 755050 |
| Cardio-Thoracic Surg | Fellow (Res) | Encounter View | 755269 |
| Hospital Medicine | Resident | Encounter View | 754791 |
| Pulmonary Med | Resident | Orders View | 754914 |
| Obstetrics | Nurse | Schedule Modify | 755145 |
| Obstetrics | Fellow (Res) | Schedule View | 755145 |
| Hospital Medicine | Resident | Encounter View | 754911 |

| Role | Access | Avg | STD | No. Access | No. Reps. |
|---|---|---|---|---|---|
| Hematology-Resident | Inpatient MAR-Exit | 1 | 0 | 1 | 1 |
| Hematology-Fellow (Res) | Meds-View | 1 | 0 | 1 | 1 |
| Hematology-Resident | LOS Section-View | 1 | 0 | 1 | 1 |
| Hematology-Fellow (Res) | SmartSet-Exit | 1 | 0 | 1 | 1 |
| Hematology-Resident | Orders-View | 4 | 3 | 8 | 2 |
| Hematology-Hospitalist | OtherEnc-View | 1 | 0 | 1 | 1 |
| Hematology-Physician | OtherEnc-View | 2 | 0 | 2 | 1 |
| Hematology-Fellow (Res) | SmartSet-View | 1 | 0 | 1 | 1 |
| Hematology-Physician | Encounter-View | 2.25 | 1.089725 | 9 | 4 |
| Hematology-Resident | OtherEnc-View | 2.636364 | 2.346089 | 29 | 11 |
| Hematology-Resident | Examroom-View | 1 | 0 | 6 | 6 |
| Hematology-Resident | Guidelines-View | 1 | 0 | 1 | 1 |
| Hematology-Fellow (Res) | Schedule-View | 2 | 0 | 2 | 1 |
| Hematology-Resident | History-View | 1 | 0 | 1 | 1 |
| Hematology-Fellow (Res) | OtherEnc-View | 1.666667 | 0.471405 | 10 | 6 |
| Hematology-Resident | Message-View | 1 | 0 | 2 | 2 |
| Hematology-Resident | Encounter-View | 1.608696 | 0.920261 | 37 | 23 |
| Hematology-Fellow (Res) | Orders-View | 3 | 1.414214 | 9 | 3 |
| Hematology-Fellow (Res) | Result Entry-View | 1 | 0 | 1 | 1 |
| Hematology-Fellow (Res) | Examroom-View | 1 | 0 | 2 | 2 |
| Hematology-Fellow (Res) | CR NOTES-View | 1 | 0 | 1 | 1 |
| Hematology-Fellow (Res) | Encounter-View | 1.5 | 1.190238 | 18 | 12 |
| Hematology-Resident | OtherEnc-Print | 1 | 0 | 2 | 2 |
| Hematology-Resident | CR NOTES-View | 1 | 0 | 4 | 4 |

FIG. 3D

HEALTHCARE PRIVACY BREACH PREVENTION THROUGH INTEGRATED AUDIT AND ACCESS CONTROL

RELATED APPLICATION

This application claims the benefit of priority from U.S. Provisional Patent Application No. 61/653,029, filed May 30, 2012, the entire contents of which are incorporated herein by reference.

TECHNICAL FIELD

The present disclosure relates generally to methods and systems for managing healthcare access and in particular for preventing healthcare privacy breach.

BACKGROUND

Several healthcare institutions store and process people's personal health data and make the data available to their employees. Hospitals, for example, store information related to the health status and treatment of their patients and provide those data to their care providers such as nurses, physicians, or staff. The medical data, however, are often very sensitive. A healthcare institution should protect the privacy of their patients by exercising care when they allow care providers access the data. In particular, many privacy laws mandate the health care providers to limit accesses to their records. For example, in the United States, the Health Insurance Portability and Accountability Act of 1996 (HIPPA) requires that hospitals protect the sensitive data in their electronic medical record systems by only allowing minimum necessary accesses to those data.

To comply with the privacy requirements, some institutions establish limited access policies. These policies limit access to some types of data or by some care providers. Some institutions establish such policies by enforcing access permissions based on a care provider's position or the provider's relationship with a patient. Some hospitals, for example, may establish access permissions that allow viewing of medical records in a department only to providers that are in that department, or allow modifying of a patient's records only to the patient's physicians and their staff. Such limited access policies, however, are often arbitrary and may not fit all scenarios in which access is needed.

Healthcare organizations, thus, often find it difficult or impractical to establish limited access policies according to the privacy laws. Organizations realize that to provide an optimum service, they may need to allow access to the data to a variety of care providers. These care providers may need to view or edit the data under different routine or emergency situations. For example, different medical providers may need to view the records of a patient to provide the patient with a service such as medication, lab test, or appointment. Additionally, in a medical emergency, a patient may be treated by any care provider and not just those that routinely treat the patient. Thus, in an emergency, any provider may legitimately need to access the patient's records.

Therefore, establishing limited access policies may add to the costs or bureaucratic overheads. In exceptional cases such as emergencies, for example, when an access is necessary but not permitted, a care provider may have to seek a special permission or request another care provider with the right permissions to access some data.

To address the shortcomings of limited access policies, some institutions establish an open access policy. According to open access policies, a large number of care providers in the organization can access or modify the records of a large number of patients. In some cases, any provider can essentially view or edit the records of any patient. Such open access policies avoid the inflexibilities of limited access policies, but open the door for abuse or breach of privacy laws.

To address the privacy issues with the open access policies, some institutions maintain access logs that record details of occasions in which a provider accesses a patient's records. The organization occasionally audits the logs, that is, reviews the access logs in search of evidence of accesses that are nefarious or violate privacy laws. Such accesses may include an occasion that a patient's record is accessed by a healthcare provider who is not directly involved with a patient's routine or emergency care and instead accesses the records for personal gains. The audits, however, are often subjective, and either costly or inefficient. The audits often result in several false negatives or false positives. The errors occur because the access logs are usually very large and searching through them is a cumbersome task. A reviewer may easily overlook an unauthorized access among a large number of legitimate accesses. Further, many accesses may seem unreasonable upon first view, but after further investigation turn out to be legitimate. For example, a care provider may need to access the records of a patient not under the provider's care for legitimate reasons such as providing advice to another provider, providing care to another patient whose treatment schedule overlaps with the first patient's treatment, or collecting statistics. Determining whether an access is legitimate or unauthorized may require resolving complex questions, a task that is often cumbersome and costly.

Many organizations, therefore, either perform inefficient audits that overlook privacy breaches, or forgo audits altogether, which will leave the organization vulnerable to privacy breaches and violation of privacy laws.

SUMMARY

In some embodiments, a computer-implemented method for compliance with a privacy requirement comprises analyzing, using one or more processors, an access log related to a history of users accessing records; deriving a plurality of roles assigned to the users and a plurality of accesses reflecting actions taken by the users; deriving from the access log a mapped log comprising a plurality of mapping records including a plurality of mapped role-access pairs; generating, using the one or more processors, a reduced log including a plurality of reduced records comprising a mapped role-access pair and statistics that are associated with the mapped role-access pair, the statistics being derived from a subset of the mapping records that include the mapped role-access pair; and deriving an access policy based on the reduced log, wherein the access policy includes a plurality of proposed role-access pairs.

In some embodiments, the method further comprises storing, in a storage device, a default access policy related to existing access permissions for the users, the default access policy including a plurality of default role-access pairs including at least one role of the roles and one or more of the accesses permitted to the one role; and performing a comparison of the default access policy with the mapped log, wherein deriving the access policy includes deriving a new access policy using a result of the comparison.

In some embodiments, the method further comprises deriving the default access policy from the access log. In some embodiments, the method further comprises receiving the default access policy as an explicit default policy.

In some embodiments, the access log includes a plurality of log entries, and wherein at least one of the mapped role-access pairs includes one role of the roles and one access of the accesses that is associated with the one role via one of the log entries.

In some embodiments, the method further comprises using the reduced log to derive a compliance score indicating a level of compliance with the privacy requirement. In some embodiments, performing the comparison includes deriving an unutilized role-access pair that is included in the default role-access pairs and is not included the mapped role-access pairs, and wherein deriving the new access policy includes removing from the default access policy the unutilized role-access pair.

In some embodiments, the statistics include an average access per user for the mapped role-access pair derived from the subset of the mapping records. In some embodiments, deriving the access policy comprises assigning to the mapped role-access pair a flag indicating underutilization if the average access per user for the mapped role-access pair is less than or equal to a threshold.

In some embodiments, the statistics further include an identification of a user associated with the mapped role-access pair and an access count for the identification indicating a number of mapping records including the mapped role-access pair and the identification, and wherein deriving the access policy comprises assigning a flag indicating abnormal frequent utilization to the identification if the access count for the identification exceeds a sum of the average access per user for the mapped role-access pair and an increase tolerance.

In some embodiments, the statistics further include an identification of a user associated with the mapped role-access pair and an access count for the identification indicating a number of mapping records including the mapped role-access pair and the identification, and wherein deriving the access policy comprises assigning a flag indicating abnormal infrequent utilization to the identification if the access count for the identification is less than the average access per user for the mapped role-access pair minus a decrease tolerance.

In some embodiments, a system for compliance with a privacy requirement comprises a mapper module configured to analyze an access log related to a history of users accessing records, to derive a plurality of roles assigned to the users and a plurality of accesses reflecting actions taken by the users, and to derive a mapped log comprising a plurality of mapping records including a plurality of mapped role-access pairs; a reducer module configured to generate a reduced log including a plurality of reduced records comprising a mapped role-access pair; and an analyzer module configured to derive statistics that are associated with the mapped role-access pair, the statistics being derived from a subset of the mapping records that include the mapped role-access pair In some embodiments, the analyzer module is further configured to derive an access policy based on the reduced log, wherein the access policy includes a plurality of proposed role-access pairs. In some embodiments, the system further comprises a storage device for storing a default access policy related to existing access permissions for the users, the default access policy including a plurality of default role-access pairs including at least one role of the roles and one or more of the accesses permitted to the one role, wherein the analyzer module is further configured to perform a comparison of the default access policy with the mapped log and derive a new access policy as the access policy using a result of the comparison. In some embodiments, the analyzer module is further configured to derive the default access policy from the access log.

In some embodiments, a non-transitory computer-readable medium stores a computer program, wherein the computer program, when executed by one or more processors, causes the one or more processors to perform a method for compliance with a privacy requirement, the method comprising analyzing, using one or more processors, an access log related to a history of users accessing records; deriving a plurality of roles assigned to the users and a plurality of accesses reflecting actions taken by the users; deriving from the access log a mapped log comprising a plurality of mapping records including a plurality of mapped role-access pairs; generating, using the one or more processors, a reduced log including a plurality of reduced records comprising a mapped role-access pair and statistics that are associated with the mapped role-access pair, the statistics being derived from a subset of the mapping records that include the mapped role-access pair; and deriving an access policy based on the reduced log, wherein the access policy includes a plurality of proposed role-access pairs.

BRIEF DESCRIPTION OF THE DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings:

FIGS. 3B-3D show exemplary logs according to some embodiments.

DETAILED DESCRIPTION

Figure 1:
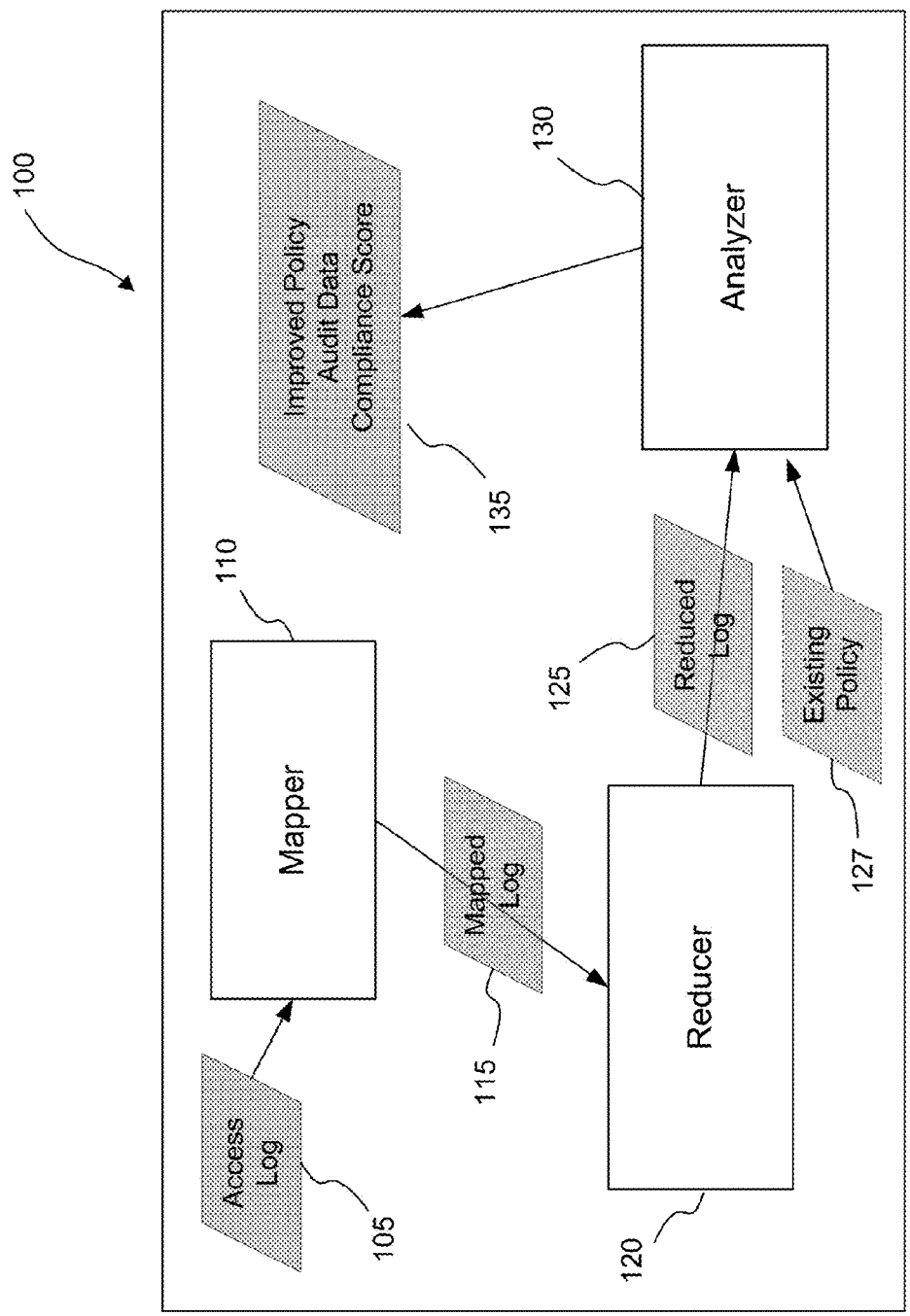
FIG. 1 is a block diagram of a privacy compliance system according to some embodiments.

The following detailed description refers to the accompanying drawings. Wherever possible, the same reference numbers are used in the drawings and the description to refer to the same or similar parts. Also, similarly named elements may perform similar functions and may be similarly designed, unless specified otherwise. Numerous details are set forth to provide an understanding of the described embodiments. The embodiments may be practiced without these details. In other instances, well-known methods, procedures, and components have not been described in detail to avoid obscuring the described embodiments. While several exemplary embodiments and features are described here, modifications, adaptations, and other implementations may be possible, without departing from the spirit and scope of the invention. Accordingly, unless stated otherwise, the descriptions relate to one or more embodiments and should not be construed to limit the invention as a whole. Instead, the proper scope of the invention is defined by the appended claims.

As used in this disclosure, a set can include one or more members and a subset of a set can include one or more than one, including all, members of the set.

Several embodiments address the requirements of the privacy policies by providing a privacy compliance system, which analyzes existing access policies and derives a new access policy. The system may receive the existing policies from an external source or may derive the existing policies from access logs, which include log entries. In various embodiments, an access log is collected by a health care provider institution, such as a hospital. In some embodiments, each log entry includes information about an instance in which a medical provider views or modifies medical records of a patient. In various embodiments, the system also analyzes access logs to derive audit data, or compliance scores indicating the level of compliance with privacy policies.

FIG. 1 is a block diagram of a privacy compliance system 100 according to some embodiments. System 100 includes a mapper module 110, a reducer module 120, and an analyzer module 130.

In some embodiments, mapper 110 receives an access log 105 and generates a mapped log 115. Mapper 110 may be configured to receive different types of access logs with different formats and derive the relevant information from each of those different formats, as detailed below. Mapper 110 may perform as an interface for the system for transforming different types of access logs to a standard format that is usable by other modules in the system. In some embodiments, mapper 110 includes a plurality of reader modules, each adapted to extract the relevant information from one type of access logs used by a specific care provider organization. In various embodiments, mapper 110 uses the information derived from the access log to generate mapped log 115. Mapper 110 may generate mapped log 115 in a standard format that is not dependent on the format of access log 105. In some embodiments, mapped log 115 includes a plurality of mapping records, each corresponding to a log entry, as detailed below. Each mapping record may include mapped role-access pair, that is, a role, and an access that is mapped to the role.

In some embodiments, reducer 120 analyzes mapped log 115 and generates one or more reduced logs 125. Reduced log 125 may include a plurality of reduced records. Each reduced record may include a mapped role-access pair and one or more items of information derived for the mapped pair, as further explained below. A reduced record may summarize various information about accesses performed by a role.

In some embodiments, analyzer 130 analyzes reduced log 125 and generates an access analysis output 135 as explained below in more detail. Analysis output 135 may include a new access policy. In some embodiments, to derive the new access policy, the system uses an existing policy 127. Existing policy 127 may indicate existing access permissions of different roles. The new policy, on the other hand, may include a modified set of permissions for different roles.

In various embodiments, access analysis output 135 also includes audit data or a compliance score, as detailed below. The audit data may include information about various types of abnormal activities derived from the access log. Further, the compliance score may assess the level of compliance of existing access policies with the privacy laws or policies.

Figure 2:
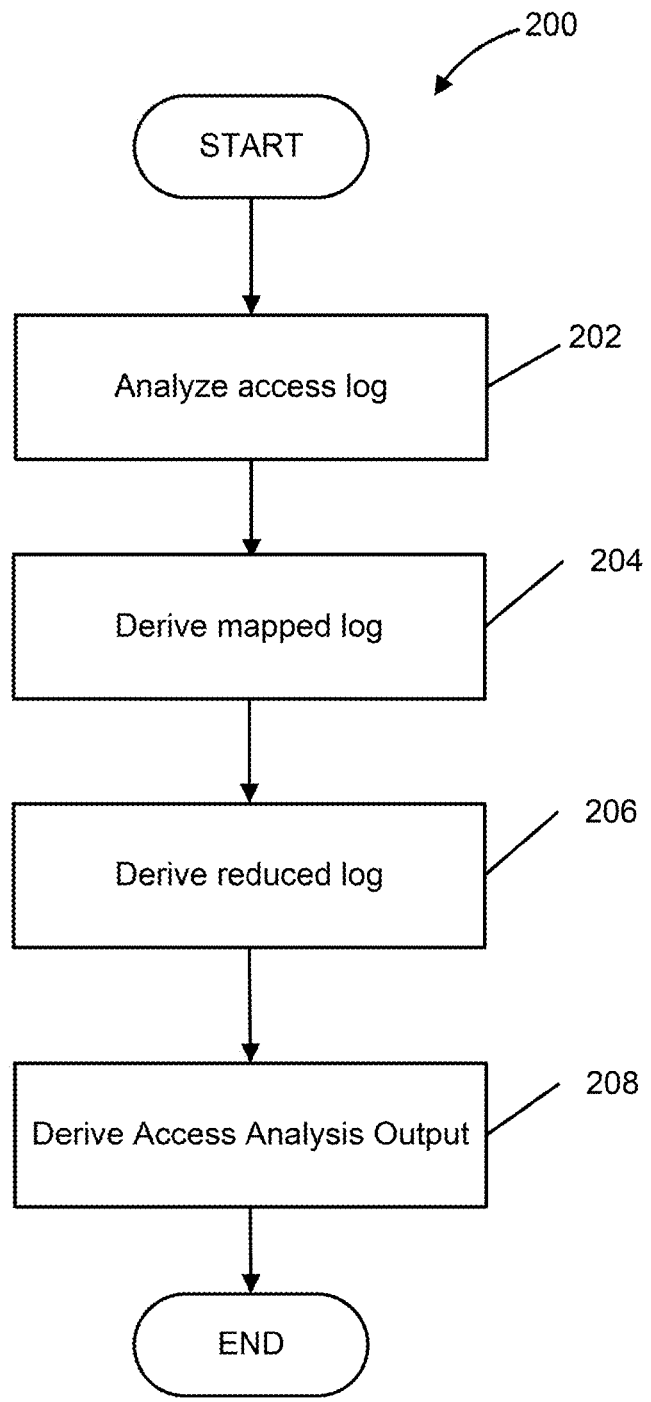
FIG. 2 shows a flowchart of a process for analyzing an access log according to some embodiments.
Figure 3A:
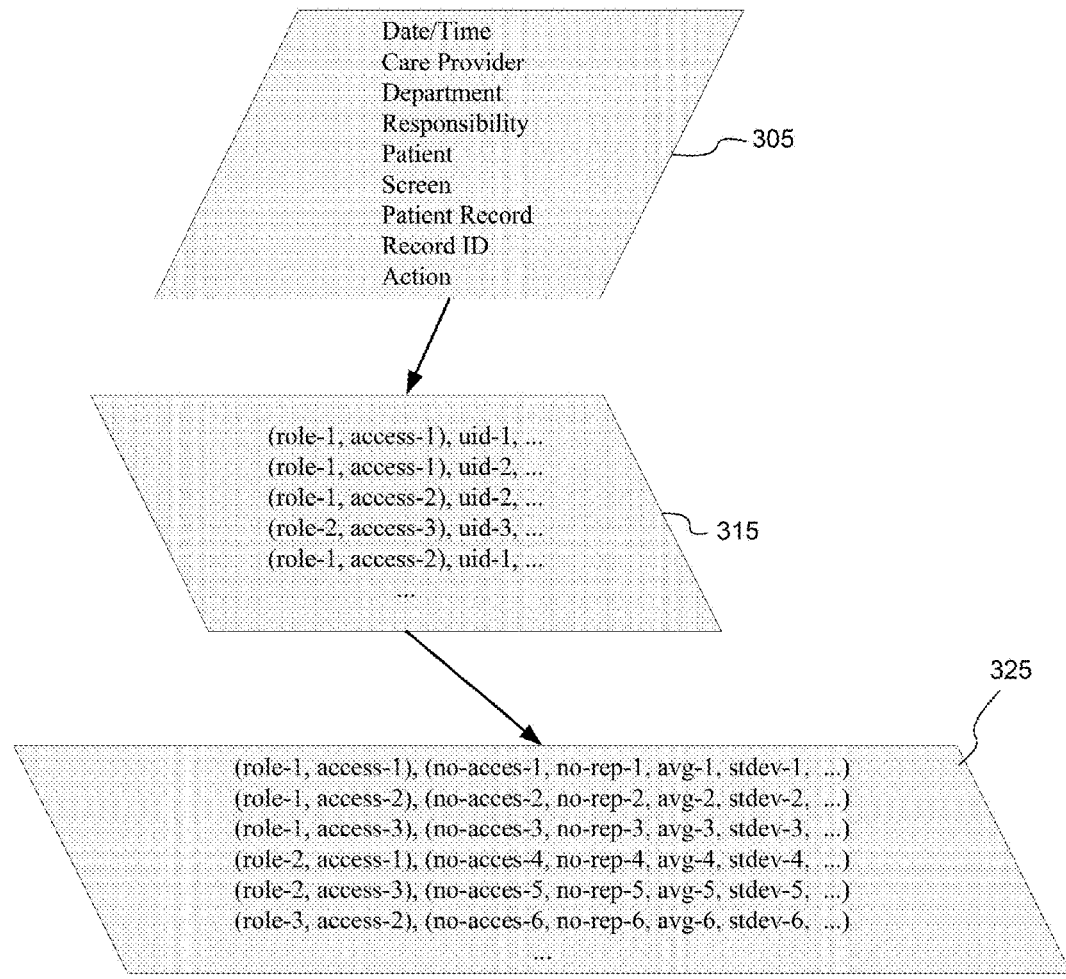
FIG. 3A shows schematics of different exemplary healthcare related data and files according to some embodiments.

FIG. 2 shows a flowchart of a process 200 for analyzing an access log according to some embodiments. Further, FIG. 3A shows schematics of exemplary data and files utilized or derived during the process of process 200 according to some embodiments. Process 200 includes various steps for processing the data of the access log and deriving information used in the analysis. In various embodiments, process 200 is performed by a system such as privacy compliance system 100 or one or more of its modules.

In block 202, the system analyzes the access log. In some embodiments, block 202 is performed by a mapper module such as mapper 110 in FIG. 1. In various embodiments, an access log includes raw data as collected by a care provider institution.

FIG. 3A shows a schematic of an exemplary access log 305 according to some embodiments. Access log 305 includes multiple log entries, each related to one instance in which someone accessed a medical record. The log entry may relate to an instance in which a care provider views or modifies the electronic records of a patient through a specific screen of a computer application. In FIG. 3A, access log 305 depicts a list of the types of data which may be included in each log entry. In this example, each log entry includes the date and time of the access, the name or identification of the care provider, the department and the responsibility of the care provider, the name or identification of the patient, the identification of the screen, the name or identification of the specific medical record, and the type of action that the provider performed on the record. In some embodiments, the department can indicate a department of a medical organization, such as a hospital; the responsibility can indicate, for example, a physician, a fellow, a surgeon, a head nurse, or a nurse; the screen can indicate, for example, medications, lab results, examination room, and visits; and the action can indicate viewing, modifying, adding, or deleting a record.

Figure 3B:

FIG. 3B shows an exemplary access log 355 according to an embodiment. Access log 355 includes 26 entries, each divided into 9 columns. The columns include multiple data for the entry, respectively consisting of patient identification, patient's age, record identification, encounter type, representative identification, date/time of access, department of the representative, responsibility of the representative, screen, and action.

Returning to FIG. 2, in block 204 the system derives a mapped log. In some embodiments, block 204 is performed by a mapper module such as mapper 110 in FIG. 1. The mapped log may be in a standard format that is not dependent on the format of the access log. The standard format of the mapped log allows various modules in the system to use the mapped log, regardless of the origin of the mapped log. In some embodiments, the mapped log may include a plurality of mapping records, each corresponding to a log entry.

FIG. 3A also shows a schematic of an exemplary mapped log 315 according to some embodiments. Mapped log 315 may include multiple mapping records, each derived from one log entry. In FIG. 3A, each line in mapped log 315 depicts one mapping record. Each mapping record includes a mapped role-access pair, which pairs a role record with an access record. Moreover, in the example of FIG. 3A, each mapping record further includes a user identification (uid) of the care provider associated with the corresponding log entry.

In various embodiments, a role record indicates the role of the care provider associated with the corresponding log entry. In some embodiments, a role record is derived by combining the department and the responsibility of the care provider. For example, in some embodiments, distinct roles can be derived by combining departments such as hematology and radiology, and responsibilities such as resident, physician, fellow, and nurse. Thus, for example, eight distinct roles may be derived as hematology-resident, hematology-physician, hematology-fellow, hematology-nurse, radiology-resident, radiology-physician, radiology-fellow, and radiology-nurse.

In various embodiments, an access record indicates a type of access associated with the log entry. In some embodiments, an access can be derived by combining the screen and the action associated with the log entry. Therefore, different accesses can be derived by combining screens such as medications, orders, examroom; with actions such as view, modify, or delete. Thus, for example, different access records can be medications-view, medications-delete, medications-modify, orders-view, orders-modify, orders-delete, examroom-view, and so on.

Each mapping record, therefore, may map a role record with an access record based on a log entry. In some embodiments, each mapping record thus indicates that, in an event recorded in a log entry, someone with the recorded role performed the recorded access. In exemplary mapped log 315, for instance, the first row includes the mapped pair (role-1, access-1) and a user identification uid-1. This mapping record, thus, indicates that based on one log entry a care provider with a user identification uid-1, for whom the role was role-1, performed an access indicated as access-1. Similarly, the fifth row indicates that based on another log entry the same care provider in the same role performed an access indicated as access-2. Further, the second row indicates that based on yet another log entry a different care provider, with user identification uid-2, who has the same role (role-1), performed the access indicated as access-1.

According to some embodiments, a role record does not depend on a specific care provider, and an access record does not depend on a specific patient. That is, for example, two care providers may be given the same role if they have the same responsibility (e.g., nurse) in the same department (e.g., radiology). Similarly, two accesses may be given the same access record if they correspond to accessing the same type of screen (e.g., medications screen) and performing the same action (e.g., viewing). Therefore, in mapped log 315, accesses indicated as access-1 in rows 1 and 2, for example, may indicate, on two different occasions, accessing the same screen and performing the same action, regardless of whether the patient records belonged to the same patient or to two different patients.

FIG. 3C shows an exemplary mapped log 365 according to an embodiment. Mapped log 365 includes 26 rows, each showing a mapping record that corresponds to an entry in access log 355 of FIG. 3B. Each mapping record includes a role, an access, and a user id. Each role is a combination of a department and a responsibility. For the first record in the first row, for example, the role is Hematology-Fellow. For the second record in the second row, on the other hand, the role is Hospital Medicine-Resident. Each access, on the other hand, is a combination of a screen and an action. For example, the access for the first record is Examroom-View, and for the second record is Encounter-View. The user id is the identification of the representative who performed the action.

Returning to FIG. 2, in block 206 the system derives a reduced log. In some embodiments, block 206 is performed by a reducer module such as reducer 120 in FIG. 1. In various embodiments, the reduced log includes a plurality of reduced records. Each reduced record may include a mapped role-access pair and one or more information items derived for that mapped pair. A reduced record may summarize various information items about accesses performed by a role.

An example of a reduced log derived in block 206 is indicated in FIG. 3A as reduced log 325. Reduced log 325 includes multiple reduced records. In FIG. 3A, each line in reduced log 325 depicts one reduced record. Each reduced record includes a mapped role-access pair and one or more reduced information corresponding to the role-access pair.

In some embodiments, the reducer derives the reduced information items from a subset of mapping records which share the same role-access pair. In reduced log 325, for example, each row includes a mapped role-access pair and some statistics derived from a subset of log entries that correspond to that pair. In FIG. 3A, the statistics in each row include a number of accesses, a number of representatives, an average, and a standard deviation. The number of accesses indicates the number of the subset of all log entries that corresponded to the role-access pair. For each role-access pair, a representative is a care provider that is responsible for at least one log entry in that subset. The number of representatives indicates the number of different care providers, i.e., with distinct user identifications, in that subset of log entries. The average indicates an average access per representative, that is, the average of the distribution of the number of log entries for each representative of the role-access pair. And the standard deviation indicates the standard deviation of that distribution.

In some embodiments, different reduced records correspond to different mapped pairs. In reduced log 325 of FIG. 3A, for example, the first row indicates that for the mapped pair (role 1, access 1), the number of accesses is a number indicated as no-acces-1, the number of representatives is a number indicated as no-rep-1, and the average and standard deviation per representative are indicated as values avg-1 and stdev-1. Similarly, the fourth row, for example, indicates that for the mapped pair (role 2, access 3), the number of accesses is no-acces-5, the number of representatives is no-rep-5, and the average and standard deviation per representative are avg-5 and stdev-5.

FIG. 3D shows an exemplary reduced log 375 according to an embodiment. Reduced log 375 includes 24 rows, each listing a reduced record indicated by a mapped role-access pair and four corresponding information for the pair. In particular, the first and second columns respectively list the role and the access in the role-access pair. The third to sixth column respectively list an average, a standard deviation, a number of accesses, and a number of representatives for the mapped pair. In the exemplary reduced log 375, the department portion of all listed roles is Hematology. In the first record, for example, the role is Hematology-Resident and the access is Inpatient MAR-Exit. For this role-access pair, the average access per representative is 1, the standard deviation of the access per representative is 0, the number of accesses is 1 and the number of representatives is 1. This data shows that, in the corresponding access log (not shown), one Hematology-Resident used the Inpatient MAR-Exit access once.

For the ninth reduced record in reduced log 375, on the other hand, the role is Hematology-Physician and the access is Encounter-View. For this role-access pair, the average access per representative is 2.25, the standard deviation is around 1.09, the number of accesses is 9, and the number of representatives is 4. This record show that 4 different physicians from the Hematology department viewed the Encounter screen for one or more patients a total of 9 times, such that the average access per physician is 2.25 with a standard deviation of 1.09.

In some embodiments, the system uses a mapper job to process rows of log entries in the access log and to generate the mapped log. Further, the system uses a reducer job to analyze the mapping records in the mapped log and to derive the reduced log. In various embodiments, a job is a scheduled map or reduce task. Also, a job may be a compound task including one or more mappers and on or more reducers.

High-level code (1), below, shows an exemplary combination of a mapper job and a reducer job according to an embodiment. The mapper job receives rows of the access log as inputs and outputs mapping records including role-access pairs and corresponding uids. Further, the reducer job receives these mapping records as inputs and outputs reduced records that include the role-access pair and various statistics discussed above.

$$\text{map(rows)} \rightarrow ((\text{role, access}), (\text{uid})) \text{ reduce } ((\text{role, access}), (\text{uid})) \rightarrow ((\text{role, access}), (\text{number of accesses, number represented, average, standard deviation})) \quad (1)$$

In some embodiments, the reducer derives and includes in the reduced log other types of statistics for role-access pairs. For each role-access pair, for example, the reducer may list the different representatives, i.e., care providers, who appear in the subset of log entries for the role-access pair. Further, for each representative, the reducer may derive a count, as the number of times that the representative appears in that subset. That is, for each role-access pair and representative, the count is the number of utilizations by the representative, that is, the number of times that the representative utilized the access in the role-access pair.

High-level code (2), below, shows an exemplary combination of a mapper job and a reducer job that derive such additional statistics according to an embodiment. In particular, in code (2) the reducer job receives the mapping records as inputs and outputs reduced records that includes, for each role-access pair, different uids (of the corresponding representatives) and counts for each representative.

$$\text{map(rows)} \rightarrow ((\text{role, access}), (\text{uid})) \text{ reduce } ((\text{role, access}), (\text{uid})) \rightarrow ((\text{role, access}), (\text{uid, count})) \quad (2)$$

Returning to FIG. 2, in block 208 the system derives an access analysis output. In some embodiments, block 208 is performed by an analyzer module such as analyzer 130 in FIG. 1. In some embodiments, the access analysis output may include a new access policy.

Figure 4:
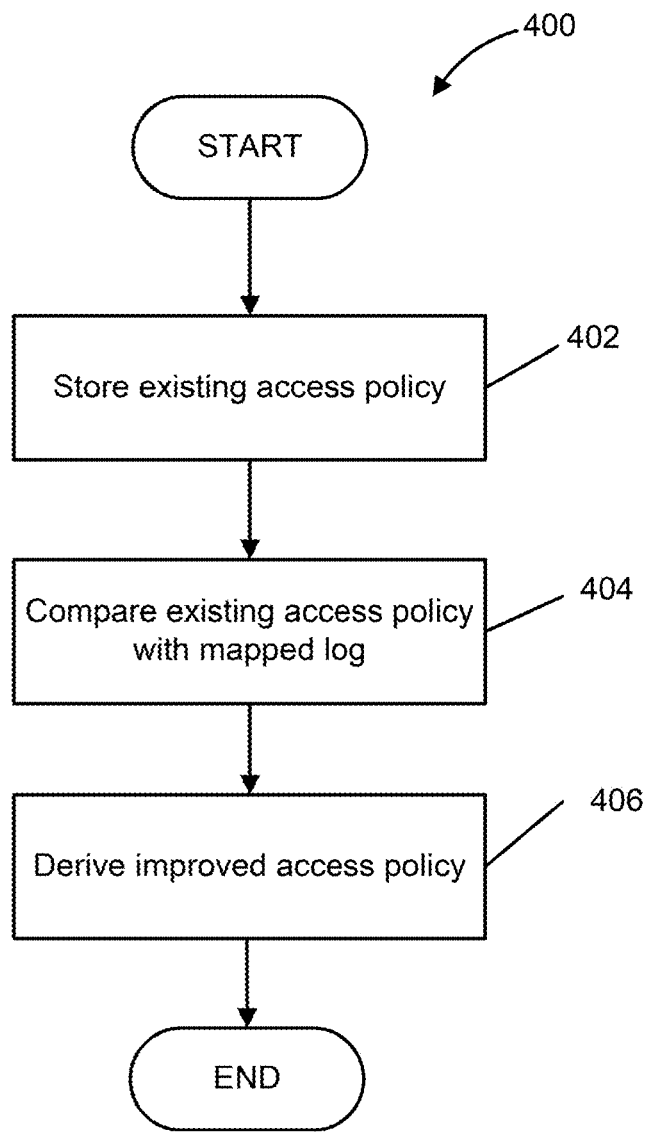
FIG. 4 shows a flowchart of a process for deriving an access policy according to some embodiments.

FIG. 4 shows a flowchart of a process 400 for deriving a new policy according to some embodiments. Process 400 includes steps for comparing an existing policy with the access records and deriving a proposed new policy. In various embodiments, process 400 is performed by a system such as privacy compliance system 100 or one or more of its modules. In some embodiments, process 400 is performed by an analyzer module, such as analyzer module 130.

In block 402, the system stores an existing access policy, such as existing policy 127. In some embodiments, the existing access policy is an access policy that is presently enforced by the care provider institution. In some embodiments, an existing policy includes a set of roles and, for each role, a set of accesses that are permitted to that role. For example, an exemplary existing policy may indicate the following access permissions for some departments: a physician can view or modify a medication record but cannot modify a visit record; a nurse can view a medication record but cannot modify or delete it; a nurse can view and modify a visit record; etc.

In some embodiments, the system derives an existing policy from the access log. In some embodiments, the mapper derives the existing policy as a default policy. The mapper may derive the default policy by cross-multiplying a subset of roles with a subset of accesses derived from the access log. That is, the default policy allows, for each role in the subset of roles, all accesses in the subset of accesses. In some embodiments, the subset of roles includes all roles and the subset of accesses includes all accesses. The default policy, thus, may be an open access policy that essentially permits any care provider in any role to perform any of the accesses. In various embodiments, the system counts the number of all allowed role-access pairs in the existing policy as the number of all mappings.

In block 404, the system compares the existing access policy with accesses actually used by the care providers. To this end, in some embodiments, the analyzer module divides the set of role-access pairs into those that are utilized and those that are not utilized. A utilized role-access pair may be a pair that appears in the access log at least once. Such a utilized pair thus appears in a mapping record in the mapped log. An unutilized pair, on the other hand, may be a pair that does not appear in the access log and, thus, not in any mapping record. Such an unutilized role-access pair indicates a role that has never used the access for which it has permission. The analyzer may derive unutilized role-access pairs by comparing entries in the mapped log or in the reduced log with allowed pairs in the existing policy. In particular, in some embodiments, the analyzer finds role-access pairs that are included in entries of the existing policy and are not included in any entry in the mapped log.

In block 406, the system derives a new access policy. In some embodiments, the system derives a new access policy by removing an unutilized role-access pair from the exiting access policy. That is, the new access policy removes the permission for the corresponding role to perform the corresponding access.

High-level code (3), below, shows an exemplary combination of a mapper job and an analyzer job for deriving an unutilized access pair according to an embodiment. In code (3), the mapper job receives the entries in the access log and derives a default set of role-access pairs by cross multiplying the set of roles with the set of accesses. Further, an analyzer job selects from this set of default role-access pairs those role pairs that do not appear in the mapped log.

$$\text{map(role, access)} \rightarrow \{\text{roles}\} \times \{\text{accesses}\} \text{reduce(role, access)} \rightarrow (\text{role, access}):(\text{role, access}) \text{ not in mapped log} \quad (3)$$

Figure 5:
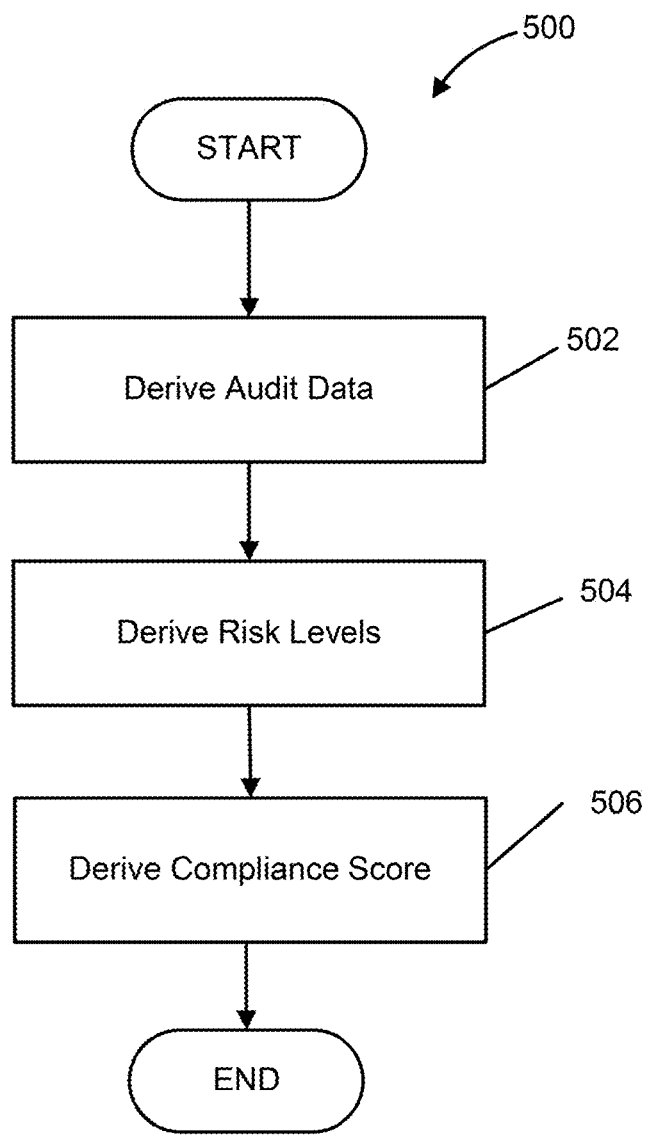
FIG. 5 shows a flowchart of a process for deriving various audit data and a compliance score according to some embodiments.

In some embodiments, the analysis output may also include audit data or a compliance score for existing access. FIG. 5 shows a flowchart of a process 500 for deriving various audit data and a compliance score according to some embodiments. In various embodiments, process 500 is performed by a system such as privacy compliance system 100 or one or more of its modules. In some embodiments, process 500 is performed by an analyzer module, such as analyzer module 130.

In block 502, the system derives the audit data. In some embodiments, the audit data includes information about abnormal access behavior reflected in the access log. Abnormal access behavior may include unutilized role-access pairs. The system may identify an unutilized role-access pair by adding an "unutilized" flag to the set of its statistics data, or by including it in an "unutilized" set. Moreover, the audit data may include a count of the unutilized pairs.

In some embodiments, in the audit data the system identifies one or more role-access pairs as "underutilized" role-access pairs. Such a role-access pair may indicate an access permission that is rarely used by the corresponding representatives. In some embodiments, the system identifies an underutilized role-access pair based on its corresponding statistics. The analyzer may identify an underutilized role-access pair as a role-access pair for which the average access per representative is low. In some embodiments, the analyzer identifies an underutilized role-access pair as a role-access pair for which the average access per representative is below a threshold value. The system may identify an underutilized role-access pair by adding a "underutilized" flag to the set of its statistics data, or by including it in an "underutilized" set. Moreover, the audit data may include a count of the underutilized pairs.

High-level code (4), below, shows an exemplary combination of a reducer job and an analyzer job for deriving an underutilized role-access pair according to an embodiment. In code (4), the analyzer job receives the reduced records, including a set of role-access pairs and the corresponding statistics. The analyzer then derives underutilized pairs as those for which the average is less than a threshold value. In some embodiments, the threshold value is chosen to be, for example, three. Thus, in this case, an underutilized role-access pair indicates an access permission that is in the average used by its representatives less than three times. In various embodiments, the threshold value is chosen based on the privacy policies. The threshold value may also be adjusted heuristically to derive a best fit with the privacy policies.

$$((\text{role, access}), (\text{average, standard deviation, count, number represented})) \rightarrow ((\text{role, access}), \text{average}): \text{average} < \text{threshold} \quad (4)$$

In some embodiments, in the audit data the system also identifies one or more role-access pairs as "underrepresented." An underrepresented pair may indicate an access that is used by a small fraction of all users who can use it. In some embodiments, the system identifies an underrepresented role-access pair from the number of its representatives. The analyzer identifies an underrepresented role-access pair as a pair for which the representatives are a small fraction of all potential representatives. In some embodiments, potential representatives are care providers who could be a representative for the pair. Potential representatives may thus be the care providers who have the same role as in the role-access pair. The system may identify an underrepresented role-access pair by adding a "underrepresented" flag to the set of its statistics data, or by including it in an "underrepresented" set. Moreover, the audit data may include a count of the underrepresented pairs. In some embodiments, some pairs are both underutilized and underrepresented. That is, some pairs may be utilized infrequently, and those infrequent utilizations are performed by a small portion of all possible representatives.

High-level code (5), below, shows an exemplary combination of a reducer job and an analyzer job for deriving an underrepresented role-access pair according to an embodiment. In code (5), the analyzer job receives the reduced records, including a set of role-access pairs and the corresponding statistics. The analyzer job then derives underrepresented pairs as those for which the ratio of the number of representatives to the total number of potential representatives is less than a probability number. In some embodiments, for example, the probability number is 10%. In these cases, therefore, an underrepresented role-access pair is a pair in which the access is used by less than 10% of the care providers that could use that access based to their role. In various embodiments, the probability number is chosen based on the privacy policies. The probability number may also be adjusted heuristically to derive a best fit with the privacy policies.

$$\text{reduce} (((\text{role, access}), \text{id}) \text{ or } ((\text{role, access}), (\text{statistical}))) \rightarrow \text{unique id}: \frac{\text{count}(\text{representatives})}{\text{count}(numberofuserswithrole)} < \text{probability} \quad (5)$$

In some embodiments, in the audit data the system also identifies one or more outlier representatives, who are representatives that use an access permission too frequently or too infrequently. A representative with an abnormal frequent utilization may be a representative who uses a permission significantly more than an average representative. Further, a representative with an abnormal infrequent utilization may be a representative who uses a permission significantly less than an average representative. In some embodiments, analyzer 130 identifies a representative with an abnormally frequent or infrequent utilization by comparing the number of times the representative used a specific access with the average access per representative. In some embodiments, a frequent utilization is identified if the number of utilizations exceeds the average access per representative by more than a multiple of the standard deviation of accesses per representative. Similarly, an infrequent utilization is identified if the number of utilizations is less than the average access per representative by more than a multiple of the standard deviation of accesses per representative.

High-level codes (6) and (7), below, show exemplary combinations of a reducer job and an analyzer job for deriving outliers, based on abnormally frequent or infrequent utilization according to an embodiment. In codes (6) and (7), the analyzer job receives the reduced records, including a set of role-access pairs, and for each role-access pair its representatives and the corresponding count for each representative. In code (6), the analyzer job then identifies an abnormally frequent utilization by a representative if the count for that representative's accesses exceeds the average access per representative by more than a multiplier times the standard deviation for that role-access pair. In code (6), the multiplier is selected to be three. In code (7), on the other hand, the analyzer job identifies an abnormally infrequent utilization by a representative if the count for that representative's accesses is below the average access per representative by more than a multiplier times the standard deviation for that role-access pair. In code (7), also, the multiplier is selected to be three. In various embodiments, the multipliers are chosen based on the privacy policies. The multipliers may also be adjusted heuristically to derive a best fit with the privacy policies.

$$\text{reduce}(\text{role, access}), \text{id}) \rightarrow ((\text{role, access}), (\text{id, utilization})): \text{utilization} > \text{average} + 3*\text{standard deviation} \quad (6)$$

$$\text{reduce}(\text{role, access}), \text{id}) \rightarrow ((\text{role, access}), (\text{id, utilization})): \text{utilization} < \text{average} - 3*\text{standard deviation} \quad (7)$$

In various embodiments, the system uses the audit data to report suspicious activities or poorly defined access rules. The user of a compliance system may use the audit data to identify care providers whose behavior requires further scrutiny. For example, in some embodiments, the user may more closely review the accesses of a provider who utilizes an access in an abnormally frequent manner. Such a high utilization may indicate that the care provider utilized the access beyond the required job activities of the provider and for nefarious purposes that violate privacy policies. Alternatively, such frequent utilization may indicate that the care provider is overworked or that the care provider's responsibilities should be divided into more than one responsibility. Similarly, a care provider that is infrequently utilizing an access may not be performing the functions necessary for the provider's role. Alternatively, such infrequent utilization may indicate that the access does not suit that provider's specific job requirements.

In some embodiments, the system uses the audit data to derive various factors related to compliance. Returning to FIG. 5, in block 504 the system derives risk levels based on audit data according to some embodiments. A risk level may indicate the risk of breaching the health privacy policies. In various embodiments, the system divides the set of existing role-access pairs into different risk color subsets and the overall risk level is derived based on the relative population of those subsets.

In some embodiments, the system derives a set of normally utilized role-access pairs from all allowed pairs. A normally utilized pair may be an allowed pair that is utilized and is not underutilized. In some embodiments, the system assigns a green risk color to normally utilized pairs.

In some embodiments, the system further assigns an orange risk color to utilized pairs that are either underutilized or underrepresented. To derive an orange count, that is, the number of pairs with an orange risk, the system may add the number of pairs in the underutilized set and in the underrepresented set, and further subtract from that sum the number of pairs that belong to both sets.

In some embodiments, to derive the orange count, the system also adds to the above calculation an adjustment factor called a D count. In various embodiments, the D count accounts for abnormalities that are not counted in some other categories. In particular, in some embodiments, the D count accounts for the number of outlier representatives, whose effect were not considered when counting underutilized or underrepresented pairs. In some embodiment, the D count is the number of outliers minus the sum of the number of underutilized and underrepresented pairs.

Moreover, in some embodiments, the system assigns a green risk color to utilized pairs that are not part of orange count. To derive the number of pairs with a green risk, the system may further subtract the D count from the number of utilized pairs.

In some embodiments, the system further assigns a red risk color to unutilized pairs.

In block 506, the system derives the overall compliance risk score based on the risk colors. In some embodiments, the system first derives an abundance ratio for each of green, orange, and red risk colors. In some embodiments, the system derives the abundance ratios by dividing the total number of pairs with each risk color by the total number of allowed pairs. In some embodiments, the system derives the abundance ratios by dividing the total number of pairs with each risk color by the total number utilized pairs. The system then may use the abundance ratios to assign a risk level to each set of risk colors.

Table (1) shows an exemplary assignment table for assigning risk levels to each risk color based on its abundance ratio. In the example of table (1), the subset of green mappings receives a high risk, if its abundance ratio is less than 75%. Similarly, the subset of orange mappings or the subset of red mappings receives a high risk level if its abundance ratio is more than 25%. Similarly, the subset of green mappings receives a medium risk level if its abundance ratio is between 75% and 90%, and it receives a low risk level if its abundance ratio is more than 90%. The subset of orange mappings or red mappings receive a medium risk level if its abundance ratio is between 10% and 25%, and receives a low risk level if its abundance is below 10%.

TABLE (1)

| Risk Level | Risk Color | | |
| --- | --- | --- | --- |
| | Green | Orange | Red |
| High | <75% | >25% | >25% |
| Medium | 75-90% | 10-25% | 10-25% |
| Low | >90% | <10% | <10% |

In some embodiments, the system derives an overall compliance score based on risk levels that it assigns to different risk colors. In some embodiment, the system derives an overall compliance score as an overall risk level. In some embodiments, the system derives an overall compliance score by finding the median of the three risk levels assigned to the three risk colors. To derive the median, the system may sort the three risk levels in increasing order, with low being the smallest, medium being in the middle, and high being the largest. The system then median by identifying the second risk level in this sorted list of three.

For instance, in one example, the green, orange, and red risk colors may have abundance ratios 70%, 13%, and 17%, respectively. Their risk levels, based on exemplary case of table (1), will thus be high, medium, and medium. Sorting this list of three risk levels will result in the sorted list {medium, medium, high}. The overall risk will be the second or median risk level, which is medium.

In another example, the green, orange, and red risk colors may have abundance ratios 88%, 7%, and 5%, respectively. Their risk levels, based on exemplary case of table (1), will thus be medium, low, and low. The sorted list will thus be {low, low, medium}, and the overall risk will be low.

Figure 6:
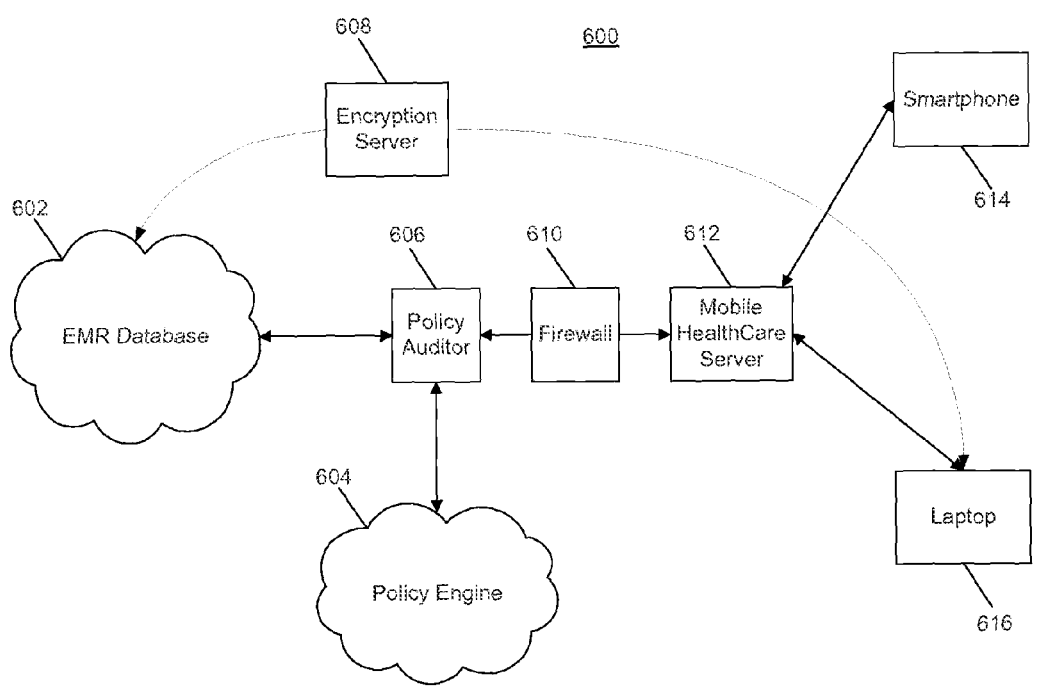
FIG. 6 depicts a healthcare privacy breach prevention system that is accessed by mobile devices according to some embodiments.

In various embodiments, the system employs a variety of technologies. FIG. 6 depicts a healthcare privacy breach prevention system 600 that is accessed by mobile devices according to some embodiments. System 600 includes an electronic medical record (EMR) database 602, a policy engine 604, a policy auditor 606, an encryption server 608, a firewall 610, a mobile healthcare server 612, and one or more mobile devices such as smartphone 614 and laptop 616. Components 602, 604, 606, 608, and 610 may be implemented as hardware, software, or both.

In various embodiments, EMR database 602 stores one or more of the access logs, mapped logs, reduced logs, and analysis output. EMR database 602 may store the data using encryption. In some embodiments, EMR Database 602 is a database used to store electronic medical records.

In some embodiments, policy engine 604 includes one or more computer processors and implements one or more of the mapper and the reducer modules. In some embodiments, policy engine 604 runs in real-time and enables accesses to be individually audited as they occur. Policy auditor 606 may also include one or more processors and may implement the analyzer module.

In some embodiments, encryption server 608 is a server enabling encryption and decryption of the data during the communications between EMR database 602 and external devices. In various embodiments, encryption server 608 is a server used to issue secure attributes to users in a given role and department. In some embodiments, attributes function similar to credentials and are issued by a centralized authority. Documents may be encrypted with a Boolean policy over a set of attributes. A user with the attributes necessary to make the policy evaluate to "True" will be able to decrypt the document.

Firewall 610 provides a barrier for controlling access to EMR database 602. Mobile healthcare server 612 provides a gateway for communications between the external devices, such as devices 614 and 616 and EMR database 602. In some embodiments, mobile healthcare server 612 includes a web interface for interaction of the administrators or the users with the system. In some embodiments, the mobile tool connects to the web interface.

Mobile devices 614 and 616 provide interfaces for users of the system to interact with the data. In particular, users may use the mobile devices to access or modify healthcare records in EMR database 602. In various embodiments, system 600 enables secure maintenance of the healthcare data, frequent auditing of those data, and improvement of access policy to minimize risk of breach, in the manner explained above.

In some embodiments, policy auditor 606 observes and proxies accesses to EMR database 602. If an access is requested, policy auditor 606 may check with policy engine 605. If policy engine 604 determines that the access is authorized, policy auditor 606 queries the database and returns the encrypted medical record, which is decrypted by the client.

In various embodiments the above operation are performed by the system in the background and invisible to the user.

In various embodiments, one or more of modules disclosed in this disclosure are implemented via one or more computer processors executing software programs for performing the functionality of the corresponding modules. In some embodiments, one or more of the disclosed modules are implemented via one or more hardware modules executing firmware for performing the functionality of the corresponding modules. In various embodiments, one or more of the disclosed modules include storage media for storing data used by the module, or software or firmware programs executed by the module. In various embodiments, one or more of the disclosed modules or disclosed storage media are internal or external to the disclosed systems. In some embodiments, one or more of the disclosed modules or storage media are implemented via a computing "cloud", to which the disclosed system connects via an internet and accordingly uses the external module or storage medium. In some embodiments, the disclosed storage media for storing information include non-transitory computer-readable media, such as a CD-ROM, a computer storage, e.g., a hard disk, or a flash memory. Further, in various embodiments, one or more of the storage media are non-transitory computer-readable media store information or software programs executed by various modules or implementing various methods or flow charts disclosed herein.

The foregoing description of the invention, along with its associated embodiments, has been presented for purposes of illustration only. It is not exhaustive and does not limit the invention to the precise form disclosed. Those skilled in the art will appreciate from the foregoing description that modifications and variations are possible in light of the above teachings or may be acquired from practicing the invention. For example, the steps described need not be performed in the same sequence discussed or with the same degree of separation. Likewise various steps may be omitted, repeated, or combined, as necessary, to achieve the same or similar objectives. Similarly, the systems described need not necessarily include all parts described in the embodiments, and may also include other parts not described in the embodiments. Accordingly, the invention is not limited to the above-described embodiments, but instead is defined by the appended claims in light of their full scope of equivalents.

What is claimed is:

1. A computer-implemented method for compliance with a privacy requirement, the method comprising:
    analyzing, using one or more processors, an access log related to a history of users accessing records;
    deriving a plurality of roles assigned to the users and a plurality of accesses reflecting actions taken by the users;
    deriving from the access log a mapped log comprising a plurality of mapping records including a plurality of mapped role-access pairs;
    generating, using the one or more processors,
        a reduced log including a plurality of reduced records comprising a mapped role-access pair and user identifications, and
        statistics that are associated with the mapped role-access pair, the statistics being derived from a subset of the mapping records that include the mapped role-access pair;
    identifying the mapped role-access pair as underrepresented based on the user identifications; and
    deriving an access policy based on the reduced log, wherein the access policy includes a plurality of proposed role-access pairs.

2. The computer-implemented method of claim 1, further comprising:
    storing, in a storage device, a default access policy related to existing access permissions for the users, the default access policy including a plurality of default role-access pairs including at least one role of the roles and one or more of the accesses permitted to the one role; and
    performing a comparison of the default access policy with the mapped log, wherein deriving the access policy includes deriving a new access policy using a result of the comparison.

3. The computer-implemented method of claim 2, further comprising deriving the default access policy from the access log.

4. The computer-implemented method of claim 2, further comprising receiving the default access policy as an explicit default policy.

5. The computer-implemented method of claim 2, wherein performing the comparison includes deriving an unutilized role-access pair that is included in the default role-access pairs and is not included the mapped role-access pairs, and wherein deriving the new access policy includes removing from the default access policy the unutilized role-access pair.

6. The computer-implemented method of claim 1, wherein the access log includes a plurality of log entries, and wherein at least one of the mapped role-access pairs includes one role of the roles and one access of the accesses that is associated with the one role via one of the log entries.

7. The computer-implemented method of claim 1, further comprising using the reduced log to derive a compliance score indicating a level of compliance with the privacy requirement.

8. The computer-implemented method of claim 1, wherein the statistics include an average access per user identification for the mapped role-access pair derived from the subset of the mapping records.

9. The computer-implemented method of claim 8, wherein deriving the access policy comprises assigning to the mapped role-access pair a flag indicating underutilization if the average access per user identification for the mapped role-access pair is less than or equal to a threshold.

10. The computer-implemented method of claim 8, wherein the statistics further include a user identification and an access count for the user identification indicating a number of mapping records including the mapped role-access pair and the user identification, and wherein deriving the access policy comprises assigning a flag indicating abnormal frequent utilization to the user identification if the access count for the user identification exceeds a sum of the average access per user identification for the mapped role-access pair and an increase tolerance.

11. The computer-implemented method of claim 8, wherein the statistics further include a user identification and an access count for the user identification indicating a number of mapping records including the mapped role-access pair and the user identification, and wherein deriving the access policy comprises assigning a flag indicating abnormal infrequent utilization to the user identification if the access count for the user identification is less than the average access per user identification for the mapped role-access pair minus a decrease tolerance.

12. A system for compliance with a privacy requirement, the system comprising:
at least one processor; and
at least one memory containing instructions that when executed by the processor, cause the system to perform the operations comprising:
analyzing an access log related to a history of users accessing records, to derive a plurality of roles assigned to the users and a plurality of accesses reflecting actions taken by the users, and to derive a mapped log comprising a plurality of mapping records including a plurality of mapped role-access pairs;
generating a reduced log including a plurality of reduced records comprising a mapped role-access pair and user identifications;
deriving statistics that are associated with the mapped role-access pair, the statistics being derived from a subset of the mapping records that include the mapped role-access pair; and
identifying the mapped role-access pair as underrepresented based on the user identifications.

13. The system of claim 12, the operations further comprising deriving an access policy based on the reduced log, wherein the access policy includes a plurality of proposed role-access pairs.

14. The system of claim 13, further comprising a storage device for storing a default access policy related to existing access permissions for the users, the default access policy including a plurality of default role-access pairs including at least one role of the roles and one or more of the accesses permitted to the one role, the operations further comprising:
performing a comparison of the default access policy with the mapped log; and
deriving a new access policy as the access policy using a result of the comparison.

15. The system of claim 14, the operations further comprising deriving the default access policy from the access log.

16. The system of claim 14, wherein performing the comparison includes deriving an unutilized role-access pair that is included in the default role-access pairs and is not included the mapped role-access pairs, and wherein deriving the new access policy includes removing from the default access policy the unutilized role-access pair.

17. The system of claim 13, wherein the statistics include an average access per user identification for the mapped role-access pair derived from the subset of the mapping records.

18. The system of claim 17, wherein deriving the access policy comprises assigning to the mapped role-access pair a flag indicating underutilization if the average access per user identification for the mapped role-access pair is less than or equal to a threshold.

19. The system of claim 17, wherein the statistics further include a user identification and an access count for the user identification indicating a number of mapping records including the mapped role-access pair and the user identification, and wherein deriving the access policy comprises assigning a flag indicating abnormal frequent utilization to the identification if the access count for the identification exceeds a sum of the average access per user for the mapped role-access pair and an increase tolerance.

20. The system of claim 17, wherein the statistics further include user identification and an access count for the user identification indicating a number of mapping records including the mapped role-access pair and the user identification, and wherein deriving the access policy comprises assigning a flag indicating abnormal infrequent utilization to the identification if the access count for the identification is less than the average access per user for the mapped role-access pair minus a decrease tolerance.

21. The system of claim 12, the operations further comprising using the reduced log to derive a compliance score indicating a level of compliance with the privacy requirement.

22. A non-transitory computer-readable medium storing a computer program, wherein the computer program, when executed by one or more processors, causes the one or more processors to perform a method for compliance with a privacy requirement, the method comprising:
analyzing, using one or more processors, an access log related to a history of users accessing records;
deriving a plurality of roles assigned to the users and a plurality of accesses reflecting actions taken by the users;
deriving from the access log a mapped log comprising a plurality of mapping records including a plurality of mapped role-access pairs;
generating, using the one or more processors,
a reduced log including a plurality of reduced records comprising a mapped role-access pair and user identifications, and
statistics that are associated with the mapped role-access pair, the statistics being derived from a subset of the mapping records that include the mapped role-access pair;
identifying the mapped role-access pair as underrepresented based on the user identifications; and
deriving an access policy based on the reduced log, wherein the access policy includes a plurality of proposed role-access pairs.

* * * * *